United States Patent [19]

Sera et al.

[11] 4,268,627

[45] May 19, 1981

[54] PHOTOGRAPHIC LIGHT-SENSITIVE MATERIAL

[75] Inventors: Hidefumi Sera; Katuzi Kitatani; Masasi Ogawa; Kunio Ishigaki; Hisashi Shiraishi, all of Minami-ashigara, Japan

[73] Assignee: Fuji Photo Film Co., Ltd., Minami-ashigara, Japan

[21] Appl. No.: 159,279

[22] Filed: Jun. 13, 1980

[30] Foreign Application Priority Data

Jun. 15, 1979 [JP] Japan .................................. 54-76161

[51] Int. Cl.³ ................................................ G03C 1/30
[52] U.S. Cl. ..................................... 430/623; 430/495; 430/539; 430/564; 430/621
[58] Field of Search ............... 430/621, 622, 623, 624, 430/625, 626, 377, 495, 546, 440, 600, 480, 613, 614, 483, 615, 486–493, 539, 542, 564

[56] References Cited

U.S. PATENT DOCUMENTS

| | | | |
|---|---|---|---|
| 3,040,047 | 6/1962 | Sirakawa | 430/489 |
| 3,185,570 | 5/1965 | Welsh | 430/489 |
| 3,586,671 | 6/1971 | Webster et al. | 430/412 |
| 3,893,862 | 7/1975 | Munshi et al. | 430/487 |
| 3,929,786 | 12/1975 | Rickter | 430/486 |

FOREIGN PATENT DOCUMENTS 1393959  5/1975  United Kingdom ................ 430/625

Primary Examiner—Mary F. Downey

Attorney, Agent, or Firm—Sughrue, Rothwell, Mion, Zinn and Macpeak

[57] ABSTRACT

A photographic light-sensitive material is described comprising at least one hydrophilic colloidal layer containing a hardener and further containing as an acid-captor at least one compound represented by formula (I) or (II):

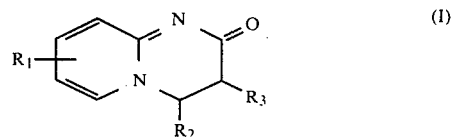

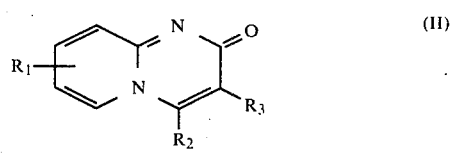

wherein $R_1$ represents hydrogen, a lower alkyl group containing 5 or less carbon atoms, an alkoxy group containing 5 or less carbon atoms, or a halogen atom, and $R_2$ and $R_3$ each independently represents hydrogen, an alkyl group containing 10 or less carbon atoms, an aryl group containing from 6 to 12 carbon atoms, or an alkoxycarbonyl group containing 5 or less carbon atoms.

9 Claims, No Drawings

PHOTOGRAPHIC LIGHT-SENSITIVE MATERIAL

BACKGROUND OF THE INVENTION

1. Field of the Invention

The present invention relates to a photographic light-sensitive material and, more particularly, to a silver halide photograhic light-sensitive material.

2. Description of the Prior Art

Photographic light-sensitive materials generally comprise, for example, a silver halide photographic light-sensitive emulsion layer, an emulsion-protecting layer, a filter layer, an interlayer, an antihalation layer, a backing layer, a film base-undercoating layer, a baryta layer, a film support, and so forth.

These layers, except for the film support, usually contain a hydrophilic colloid, such as gelatin, as a carrier.

These light-sensitive materials containing a hydrophilic colloid (hereinafter the hydrophilic colloid is described by referring to "gelatin," which is a typical example thereof) are processed with various aqueous solutions differing in pH and/or temperature. However, the gelatin layer has a poor water resistance, and hence it has a tendency to swell so much in the aqueous solution that its mechanical strength is reduced, and, in an extreme case, it will be dissolved into the processing solution. This is a fatal defect as a layer constituting a photographic light-sensitive material.

It is well known to use compound for forming cross-linkages, called "hardeners," so as to improve the physical properties of gelatin.

Many compounds have been proposed as hardeners, such as, for example, aldehydes, active halogens, aziridines, epoxides, alkanesulfonic acid esters, active vinyl compounds, dehydrating condensers (e.g., dicyclohexylcarbodiimide, etc.), and the like.

However, these compounds are not fully suitable as hardeners for photographic light-sensitive materials.

For example, aldehydes cause fogging of light-sensitive nuclei due to their reducing properties. Aziridine compounds cause serious problems in their production or application due to their detrimental actions on the human body. Other compounds also impose various restrictions due to poor stability, difficulty in preparation, etc. Thus, there are not necessarily many practically valuable hardeners.

It is well known that active halogen compounds, such as methanesulfonic acid esters, active vinyl group-containing compounds, active carboxylic acid esters, and the like, are comparatively advantageous. For example, dichlorotriazine, described in U.S. Pat. No. 3,325,287, methanesulfonic acid esters described in U.S. Pat. No. 3,834,902, vinylsulfonyl group-containing compounds described in U.S. Pat. No. 3,490,911 and German Pat. application (OLS) No. 2,749,260, active esters described in U.S. Pat. No. 3,542,558, and the like are fairly good hardeners.

However, the hardeners described here are only one of many additives used in photographic light-sensitive materials, which typically include complicated combinations of numerous components.

That is, photographic light-sensitive materials are constituted by combinations of many additives such as silver halide emulsions, chemical sensitizers, optical sensitizers, antifogging agents, surfactants, color formers, etc., and thus even slight environmental changes can often lead to serious deterioration of important properties.

Hardeners have heretofore been used as necessary ingredients for photographic light-sensitive materials, but even the few good hardeners as described above cause a reduction in the pH with the progress of cross-linking reaction which is the essential characteristic of such hardeners. In fact, measurement of pH of the film reveals that all of the foregoing hardeners reduce pH.

Hardeners in the photographic light-sensitive materials which react with an amino group of gelatin in conventional pH ranges may, though quite rarely, react with a carboxy group of gelatin to increase pH in the extremely low pH range (e.g., pH of 2 to 3).

This reduction in pH exerts serious influences on the properties of photographic light-sensitive materials. The most serious of these are reduction in sensitivity, which is of critical importance in photographic light-sensitive materials, and regression of latent image become more by the reduction in pH. It is not a fundamental solution to these problems to raise the initial pH in order to avoid the reduction in sensitivity and regression of latent image caused by the reduction in pH with the lapse of time, because raising the pH initially causes an increase in fogging and a deterioration of color image preservability.

In addition, the reduction in the pH with the progress of the cross-linking reaction delays the hardening reaction itself, thus causing so-called "post hardening", which is a change in film properties due to hardening over a long period of time, and causes a reduction in attained hardness, apparently due to self-catalytic action of deterioration of the hardener.

SUMMARY OF THE INVENTION

As a result of many investigations on the above-described problems with the hydrophilic colloidal layers of photographic light-sensitive materials resulting from the reduction in pH, it has now been discovered that these problems can be solved by using as a hardener at least one compound represented by the formula (I) or (II):

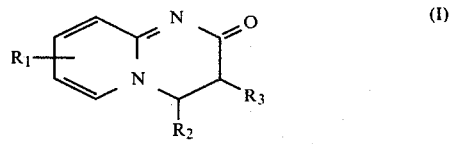

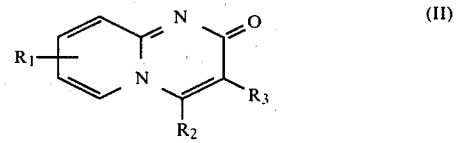

wherein $R_1$ represents hydrogen, a lower alkyl group containing 5 or less carbon atoms (e.g., a methyl group, an ethyl group, or the like), an alkoxy group containing 5 or less carbon atoms (e.g., a methoxy group, an ethoxy group, or the like), or a halogen atom (e.g., Cl, Br, or the like), and $R_2$ and $R_3$ each independently represents hydrogen, an alkyl group containing 10 or less carbon atoms (e.g., a methyl group, a butyl group, or the like), an aryl group containing from 6 to 12 carbon atoms (e.g., a phenyl group, or the like), or an alkoxycarbonyl group containing 5 or less carbon atoms.

DETAILED DESCRIPTION OF THE INVENTION

The compounds represented by the general formula (I) can be in a form wherein separate charges exist as represented by formula (IA), viz.,

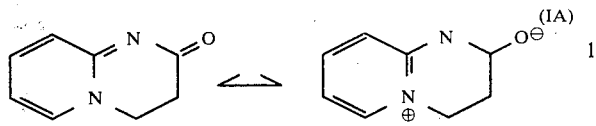

This indicates that the compounds of this invention can function as a captor for organic or inorganic acids, as illustrated in formula (IB),

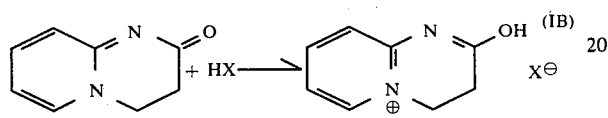

wherein $X^\ominus$ represents an acid anion.

In fact, *Chemistry Letters* (1976), pp. 13–14 reports that such compounds function as an acid captor (also referred to as the acid-capturing compound).

As has been described hereinbefore, photographic light-sensitive materials are of an extremely complicated nature, and, although many phenomena in such systems are not well understood, the effect of this compound discovered in this invention seems to result from an acid-capturing action.

In addition, there are several other advantages, which may be attributed to the acid-capturing (pH-maintaining) action, such as: (1) the cross-linking rate of the hardener is improved, thus controlling change of the hardening reaction over the lapse of a long period of time, so-called post hardening; and (2) the efficiency of the hardening reaction is improved, by preventing the self-catalytic deterioration due to change in pH.

Some of acid-capturing compounds used in this invention are known and the others are novel, and can be readily synthesized according to the conventional processes disclosed, for example, in *J. Amer. Chem. Soc.*, Vol. 74, pp. 5491–5497 (1952).

As far as is known, no utility of the above compounds has been reported yet.

Examples of the compounds that can be used in this invention, and examples for synthesizing said compounds, will be described below which, however, are not intended to limit the invention in any way.

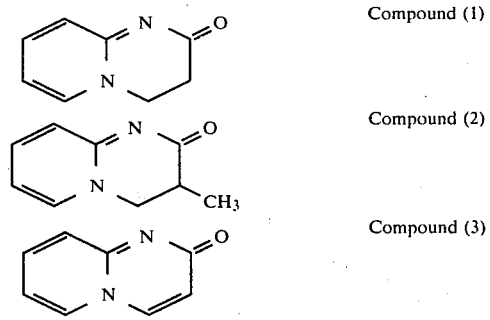

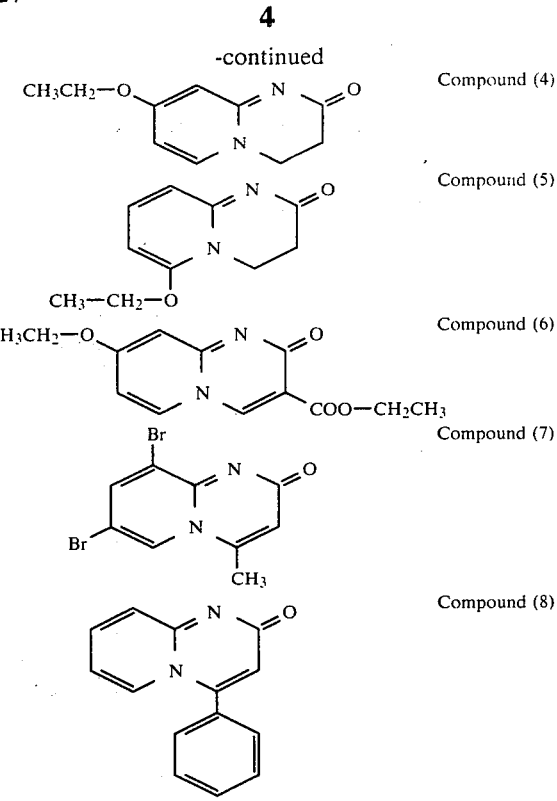

SYNTHESIS EXAMPLE 1

Synthesis of Compound 1

4.7 g of 2-aminopyridine, 5.5 g of ethyl acrylate, and 0.1 g of t-butylcatechol were heated for 8 hours in a steam bath. After the reaction, the reaction product was dissolved in methanol and, after decoloring with active carbon, the product was concentrated under reduced pressure until crystals began to be formed, followed by adding ligroin thereto to precipitate crystals. The crystals were collected by filtration and dried to obtain 4.2 g (yield: 57%) of the crystals. m.p. 186°–187° C.

SYNTHESIS EXAMPLE 2

Synthesis of Compound 3

14.4 g of 2-aminopyridine, 22.7 g of α-bromoacrylic acid, and 0.8 g of t-butylcatechol were dissolved in 220 ml of chloroform while heating, followed by refluxing for 12 hours while heating. After cooling the reaction mixture, the reaction product was collected by filtration and recrystallized from ethanol. 15.2 g of the thus obtained 2H-pyrido[1,2-a]pyrimidin-2-one hydrobromide was dissolved in 50 ml of water and neutralized with a sodium hydroxide solution. The resulting solution was concentrated to dryness, followed by extracting with a mixed solvent of chloroform and ethanol. After being concentrated, the extract was cooled to obtain 8.2 g of crystals. m.p. 248°–250° C.

The acid-capturing compound used in this invention can be added in the hydrophilic colloical layer comprising a hardener and/or the layer adjacent thereto, and it can preferably be added in the hydrophilic colloidal layer comprising a hardener.

The amount of the acid-capturing compound used according to the invention is selected according to the end-use. Usually, they can be used in amounts ranging from about 0.01 to 20 wt%, based on the total weight of dry gelatin in the photographic material. Particularly preferably, the acid-capturing compounds are used in amounts ranging from 0.1 to 10 wt%. If the amount of the compound of the present invention exceeds 20 wt% based on the total weight of dry gelatin in the photographic material, they will be dissolved away upon processing or deteriorate adhesion resistance. On the other hand, if the amount is less than 0.01 wt%, the resulting effect will be insufficient.

The compounds of the present invention may be used alone or in combination. Where the compounds of the invention are used in combination, the proportion is again selected according to the end-use of intended effects.

The hydrophilic colloidal layer of the invention contains an inorganic or organic hardener. For example, there can be used, alone or in combination, chromium salts (e.g., chromium alum, chromium acetate, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloylhexahydro-s-triazine, bis(-vinylsulfonyl)methyl ether, etc.), active halogen compounds (e.g., 2,4-dichloro-6-hydroxy-s-triazine, etc.), mucohalogenic acids (e.g., mucochloric acid, mucophenoxychloric acid, etc.), isoxazoles, dialdehydostarch, 2-chloro-6-hydroxytriazinylated gelatin, and the like. Specific examples thereof are described in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,490,911, 3,539,644, 3,543,292, 3,834,902, British Pat. Nos. 676,628, 825,544, 1,270,578, West German Pat. Nos. 872,153, 1,090,427, West German patent application (OLS) No. 2,749,260, Japanese Patent Publication Nos. 7133/59, 1872/71, etc.

The hardener is typically used in the photographic light-sensitive materials of the invention in amounts ranging from 0.01 to 20 wt%, particularly preferably 0.1 to 10 wt%, based on the weight of the gelatin.

A typical example of a binder forming the hydrophilic colloidal layer to which the compound of this invention is applied is gelatin. As for the gelatin, any of the so-called alkali-processed (or lime-processed) gelatins (i.e., those having been processed in an alkali bath before being extracted), acid-processed gelatins (i.e., those having been dipped in an acid bath), and enzyme-processed gelatins, as described in *Bull. Soc. Sci. Photo. Japan*, No. 16, p. 30 (1966), can be used. Furthermore, the compounds of the invention can be applied to low molecular gelatin, prepared by heating gelatin in a water bath or by acting thereon with protease to partly hydrolyze the gelatin.

The gelatin to which the compound of the invention is applied may, if desired, by partly replaced by colloidal albumin, casein, cellulose derivatives (e.g., carboxymethyl cellulose, hydroxyethyl cellulose, etc.), sugar derivatives (e.g., agar-agar, sodium alginate, starch derivatives, etc.), synthetic hydrophilic colloids (e.g., polyvinyl alcohol, poly-N-vinylpyrrolidone, polyacrylic acid copolymer, polyacrylamide or the derivative or partly hydrolyzed product thereof. In addition, the gelatin may be replaced by so-called gelatin derivatives, i.e., gelatin processed and modified with a reagent having a group capable of reacting with the functional groups contained in gelatin molecula (i.e., amino groups, imino group, hydroxy groups, or carboxy groups), or by a graft polymer prepared by grafting a molecular chain of another high molecular substance onto gelatin.

As for the gelatin derivatives, those that can be used include gelatin derivatives prepared by reacting gelatin with, for example, acid halides, acid anhydrides, isocyanates, bromoacetic acid, alkanesultones, vinylsulfonamides, maleinamides, maleinimides described in U.S. Pat. No. 3,186,846, acrylonitriles as described in U.S. Pat. No. 2,594,293, polyalkyleneoxides described in U.S. Pat. No. 3,312,553, epoxy compounds described in Japanese Patent Publication No. 26845/67, acid esters as described in U.S. Pat. No. 2,763,639, alkanesultones described in British Pat. No. 1,033,189, and the like.

As to the branch high polymers to be grafted on gelatin, many descriptions are given in U.S. Pat. Nos. 2,763,625, 2,831,767, 2,956,884, *Polymer Letters*, 5, 595 (1967), *Phot. Sci. Eng.*, 9, 148 (1965), *J. Polymer Sci.*, A-1, 9, 3199 (1971), and the like, Homopolymers or copolymers of those which are generally called vinyl monomers, such as acrylic acid, methacrylic acid, ester, amide or nitrile derivatives thereof, styrene, etc., can be used.

A silver halide emulsion used according to this invention is typically prepared by mixing a solution of a water-soluble silver salt (e.g., silver nitrate, etc.) with a solution of water-soluble halide (e.g., potassium bromide, etc.) in the presence of a solution of a water-soluble high polymer such as gelatin. As the silver halide, mixed silver halides such as silver chlorobromide, silver bromoiodide, silver chlorobromoiodide, etc., may be used, as well as silver chloride and silver bromide.

These silver halide grains may be of cubic form, octahedral form, or the mixed form thereof. Particle size and mean particle size distribution of the grains are not particularly limited and may be freely selected.

Various additives known in the art can be used in the above-described silver halide emulsion.

For example, gold compounds such as chloroauric acid salts, auric chloride, etc., salts of noble metals such as platinum, rhodium, palladium, iridium, etc., sulfur compounds, stannous salts, amines, and the like can be used as chemical sensitizers; cyanines, merocyanines, and carbocyanines can be used as spectral sensitizers; heterocyclic compounds including 4-hydroxy-6-methyl-1,3,3a,7-tetrazaindene, 3-methylbenzothiazole, 1-phenyl-5-mercaptotetrazole, etc., mercury-containing compounds, mercapto compounds, metal salts, etc., can be used as antifogging agents; and 4-equivalent diketomethylene series yellow couplers, 2-equivalent diketomethylene series yellow couplers, 4- or 2-equivalent pyrazolone series magenta couplers or indazole series magenta couplers, $\alpha$-naphtholic cyan couplers, phenolic cyan couplers, etc., can be used as color couplers.

In the silver halide emulsion layers and other hydrophilic colloidal layers, surfactants, matting agents, dyes, polymer latexes, etc., which are typically employed in photographic materials can also be used.

As a surfactant, natural surfactants (e.g., saponin, etc.), nonionic surfactants of alkylene oxide series, glycerol series or glycidol series, cationic surfactants (e.g., higher alkylamines, quaternary ammonium salts, heterocyclic compounds (e.g., pyridine, etc.), phosphoniums or sulfoniums, etc., anionic surfactants having acidic group such as carboxylic acid group, sulfonic acid group, phosphoric acid group, sulfuric ester group, phosphoric ester group, etc., and amphoteric surfactants (e.g., amino acids, aminosulfonic acids, aminoalcohol esters of sulfuric acid or phosphoric acid, etc., can be used. As the matting agent, water-insoluble particles of organic or inorganic compounds, such as polymethyl methacrylate particles or silicon dioxide particles having a mean particle size of $0.2\mu$ to $10\mu$, can be used. As the polymer latex, water-dispersible vinyl compounds, such as alkyl acrylate, can be used.

The use of the above-described additives to the silver halide photographic light-sensitive material of the invention and processes for preparing them are described, for example, in *Research Disclosure*, Vol. 176, pp. 22–31 (Dec., 1978).

The invention will now be described in more detail by the following examples of preferred embodiments of the present invention which, however, do not limit the invention in any way.

EXAMPLE 1

To a gelatin aqueous solution containing 70 g of dry gelatin in 1 liter of the solution, an acid-capturing compound of the invention and the hardener were added as shown below, and uniformly coated in a dry thickness of about $6\mu$ on an undercoated polyethylene terephthalate support, and dried to prepare samples. These samples were left while maintaining at 25° C. and in humidity of 50% RH and, after the first, seventh and fourteenth days after the coating, respective samples were taken out to measure the swelling ratio (Q) in 25° C. water determined according to the following formula:

$$Q = \frac{\text{Thickness increased by swelling}}{\text{Dry thickness of the film}} \times 100$$

Also, each sample was dipped in water, a needle with a steel ball of 0.4 mm in radius at the tip was pressed against the sample surface, and the load to the needle was continuously changed from 0 to 200 g while moving the needle at a velocity of 2.5 mm/sec on the sample film in a parallel direction, thus determining the needle load at which flaws form on the surface of the sample. Results thus obtained are shown in Table 1.

In Table 1, compounds (a) and (b) are those specified below:

Compound (a): 2,4-Dichloro-6-hydroxy-s-triazine sodium salt
Compound (b): $CH_2=CH-SO_2-CH_2CH_2CH_2-SO_2CH=CH_2$ As will be seen from the results of Table 1, the acid-capturing compounds of the invention improve the cross-linking rate of the hardener without inhibiting its ability to harden gelatin film within the swelling range acceptable for photographic materials, and do not cause changes in the degree of hardening with the lapse of time, i.e., so-called post hardening.

TABLE 1

| Sample No. | Compound | Amount Added (mmol/g-gelatin) | Swelling Degree 1 Day | Swelling Degree 7 Days | Swelling Degree 14 Days | Flaw-Resisting Strength (7 days after coating) (g) |
|---|---|---|---|---|---|---|
| 1 | Control | 0 | 1,000 | 1,000 | 1,000 | 7 |
| 2 | Compound (a) | 0.05 | 540 | 380 | 350 | 107 |
|   | Compound (1) | 0.33 | | | | |
| 3 | Compound (a) | 0.05 | 595 | 395 | 355 | 101 |
|   | Compound (3) | 0.33 | | | | |
| 4 | Compound (b) | 0.05 | 435 | 335 | 320 | 120 |
|   | Compound (1) | 0.33 | | | | |
| 5 | Compound (b) | 0.05 | 485 | 350 | 325 | 109 |
|   | Compound (3) | 0.33 | | | | |
| 6 | Compound (a) | 0.05 | 850 | 500 | 340 | 72 |
| 7 | Compound (b) | 0.05 | 695 | 450 | 320 | 83 |

EXAMPLE 2

To a high speed negative photographic emulsion prepared in a conventional manner and containing 120 g gelatin and 65 g silver bromoiodide per kg of the emulsion, a compound of the invention and a hardener were added as shown in the following table, and uniformly coated to form a dry thickness of $10\mu$ on an undercoated cellulose triacetate film and dried to prepare samples.

Then, after being left for 7 days at room temperature, each sample was subjected to the measurement of swelling ratio in 25° C. water in the same manner as in Example 1. The thus obtained film samples were sensitometrically exposed to a step wedge, developed at 20° C. for 8 minutes using a D-76 (a prescription published by Eastman Kodak, Co.) developer, fixed, washed, dried, and subjected to sensitometry to determine sensitivity and fog (Table 2).

As compared with the samples containing only the hardener, the samples in accordance with this invention attained a stable swelling ratio in a shorter time, thus remarkably improving the so-called post hardening properties.

As will be seen from Table 2, the samples obtained according to the present invention suffered less change in relative sensitivity and fog under various temperature and humidity conditions than the samples contained only the hardener or with other combinations, thus showing well-balanced photographic properties for materials according to this invention.

TABLE 2

| Sample No. | Compound | Amount Added (mmol/g-gelatin) | Immediately after Coating *1 | Immediately after Coating Fog | Under Accelerating Conditions (50° C., 2 days) *1 | Under Accelerating Conditions (50° C., 2 days) Fog | Swelling Ratio after 7 Days |
|---|---|---|---|---|---|---|---|
| 8 | Control | 0 | 100 | 0.05 | 100 | 0.10 | 945 |
| 9 | Compound (a) | 0.05 | 94 | 0.05 | 93 | 0.06 | 365 |
|   | Compound (1) | 0.33 | | | | | |
| 10 | Compound (a) | 0.05 | 93 | 0.06 | 92 | 0.07 | 385 |
|   | Compound (3) | 0.33 | | | | | |
| 11 | Compound (b) | 0.05 | 94 | 0.05 | 93 | 0.07 | 330 |

TABLE 2-continued

| Sample No. | Compound | Amount Added (mmol/g-gelatin) | Immediately after Coating *1 | Fog | Under Accelerating Conditions (50° C., 2 days) *1 | Fog | Swelling Ratio after 7 Days |
|---|---|---|---|---|---|---|---|
|  | Compound (1) | 0.33 |  |  |  |  |  |
| 12 | Compound (a) | 0.05 | 88 | 0.04 | 87 | 0.05 | 495 |
| 13 | Compound (b) | 0.05 | 90 | 0.05 | 89 | 0.07 | 440 |

*1 Relative sensitivity.

EXAMPLE 3

A silver bromoiodide emulsion containing 3.0 mol% silver iodide was prepared and subjected to after ripening in the presence of sodium thiosulfate and a gold salt, so as to obtain a high speed negative emulsion having maximum sensitivity This emulsion was mixed with a coupler emulsion prepared by dissolving 1-(2',4',6'-trichlorophenyl)-3-[3''-(2''',4'''-di-t-amylphenoxyacetamido)benzamido]-5-pyrazolone in a mixture of dibutyl phthalate and tricresyl phosphate and emulsifying and dispersing the resulting solution in a gelatin solution as an oil in water emulsion using sorbitan monolaurate, sulfonated oil, and sodium dodecylbenzenesulfonate as a dispersing and emulsifying agent. Then, an acid-capturing compound of this invention and the hardener were added thereto as shown in Table 3, and uniformly coated to form a dry thickness of about 10μ on an undercoated cellulose triacetate base to obtain a color film for experimental use having a single magenta layer.

This experimental color film was sensitometrically exposed to a step wedge and subjected to color development using 4-amino-3-methyl-N-ethyl-β-hydroxyethylaniline sesquisulfonate monohydrate as a developing agent to examine coloration properties through sensitometry in a manner similar to Example 2 of British Patent Application No. 2,029,977A. Density of the magenta dye thus formed was measured (at 547 nm) and relative values of the sensitivity expressed in terms of exposure amount providing an optical density of fog+0.2 are tabulated in Table 3. Also, the swelling ratio in 25° C. water was measured in the same manner as in Example 1 after leaving each sample for seven days at room temperature.

TABLE 3

| Sample No. | Compound | Amount Added (mmol/g-gelatin) | Photographic Properties Fog | Relative Sensitivity | Swelling Ratio (7 days after coating) |
|---|---|---|---|---|---|
| 14 | Control | 0 | 0.20 | 100 | 900 |
| 15 | Compound (a) | 0.05 |  |  |  |
|  |  |  | 0.20 | 99 | 235 |
|  | Compound (1) | 0.33 |  |  |  |
| 16 | Compound (b) | 0.05 |  |  |  |
|  |  |  | 0.20 | 99 | 210 |
|  | Compound (1) | 0.33 |  |  |  |
| 17 | Compound (a) | 0.05 | 0.19 | 97 | 280 |
| 18 | Compound (b) | 0.05 | 0.19 | 98 | 265 |

As will be seen from Table 3, the samples obtained according to this invention suffered less change in relative sensitivity and fog than the samples hardened singly with the hardener or by other combination, thus showing well-balanced photographic properties without inhibiting color-forming properties of the coupler and without forming color stains.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising at least one hydrophilic colloidal layer containing a hardener, and further containing as an acid-captor at least one compound represented by formula (I) of formula (II):

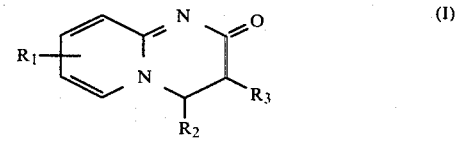

(I)

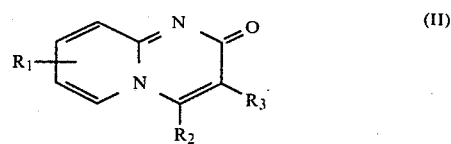

(II)

wherein $R_1$ represents hydrogen, a lower alkyl group containing 5 or less carbon atoms, an alkoxy group containing 5 or less carbon atoms, or a halogen atom, and $R_2$ and $R_3$ each independently represents hydrogen, an alkyl group containing 10 or less carbon atoms, an aryl group containing from 6 to 12 carbon atoms, or an alkoxycarbonyl group containing 5 or less carbon atoms.

2. A photographic light-sensitive material containing an acid-capturing compound as in claim 1, wherein $R_1$ is a methyl group, an ethyl group, a methoxy group, an ethoxy group, Cl or Br, and $R_2$ and $R_3$ each independently represents a methyl group, a butyl group, or a phenyl group.

3. A photographic light-sensitive material comprising at least one hydrophilic layer containing a hardener, an acid-capturing agent consisting of at least one compound represented by formula (I):

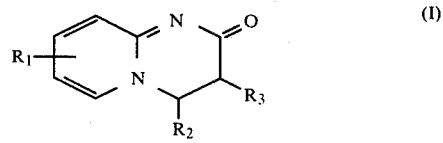

(I)

wherein $R_1$ represents hydrogen, a lower alkyl group containing 5 or less carbon atoms, an alkoxy group containing 5 or less carbon atoms, or a halogen atom, and $R_2$ and $R_3$ each independently represents hydrogen, an alkyl group containing 10 or less carbon atoms, an aryl group containing from 6 to 12 carbon atoms, or an alkoxycarbonyl group containing 5 or less carbon atoms.

4. A photographic light-sensitive material comprising at least one hydrophilic layer containing a hardener, an acid-capturing agent consisting of at least one compound represented by formula (II):

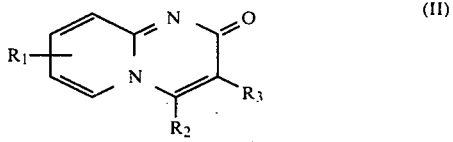

wherein $R_1$ represents hydrogen, a lower alkyl group containing 5 or less carbon atoms, an alkoxy group containing 5 or less carbon atoms, or a halogen atom, and $R_2$ and $R_3$ each independently represents hydrogen, an alkyl group containing 10 or less carbon atoms, an aryl group containing from 6 to 12 carbon atoms, or an alkoxycarbonyl group containing 5 or less carbon atoms.

5. A photographic light-sensitive material as in claim 1, 2, 3 or 4, wherein the amount of the acid-capturing agent is in the range of from about 0.01 to 20 wt%, based on the total weight of dry gelatin.

6. A photographic light-sensitive material as in claim 5, wherein the amount of acid-capturing agent is in the range of from 0.1 to 10 wt%.

7. A photographic light-sensitive material as in claim 1, 2, 3 or 4, wherein said hydrophilic colloid layer is gelatin.

8. A photographic light-sensitive material as in claim 5, wherein said hydrophilic colloid layer is gelatin.

9. A photographic light-sensitive material as in claim 6, wherein said hydrophilic colloid layer is gelatin.

* * * * *